(12) United States Patent
Van Hooser

(10) Patent No.: US 7,124,755 B2
(45) Date of Patent: Oct. 24, 2006

(54) RESPIRATORY CIRCUIT SUPPORT ARM

(75) Inventor: D. Theron Van Hooser, Salt Lake City, UT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 775 days.

(21) Appl. No.: 10/037,463

(22) Filed: Dec. 21, 2001

(65) Prior Publication Data

US 2003/0116167 A1   Jun. 26, 2003

(51) Int. Cl.
*A61G 15/00* (2006.01)

(52) U.S. Cl. ............ 128/845; 128/202.27; 128/204.18; 128/205.13; 128/846; 128/207.11; 128/DIG. 26; 248/479; 248/481; 248/49; 248/68.1; 248/176.1; 248/186.1; 248/178.1; 248/184.1

(58) Field of Classification Search ........... 128/202.27, 128/204.18, 205.13, 845, 846, 207.11, DIG. 26; 248/479, 481, 49, 68.1, 176.1, 186.1, 178.1, 248/184.1

See application file for complete search history.

(56) References Cited

U.S. PATENT DOCUMENTS

| | | | |
|---|---|---|---|
| 2,419,860 A | 4/1947 | Urrutia | |
| 3,638,973 A | 2/1972 | Poletti | |
| 3,971,538 A * | 7/1976 | Marvich | 248/278.1 |
| 4,020,834 A | 5/1977 | Bird | |
| 4,166,602 A * | 9/1979 | Nilsen et al. | 248/280.11 |
| 4,393,728 A | 7/1983 | Larson et al. | |
| 4,402,481 A * | 9/1983 | Sasaki | 248/282.1 |
| 4,427,382 A | 1/1984 | Hoffmeister et al. | |
| 4,466,307 A * | 8/1984 | Kouno | 74/479.01 |
| 4,491,435 A * | 1/1985 | Meier | 403/55 |
| 4,494,417 A | 1/1985 | Larson et al. | |
| 4,502,478 A | 3/1985 | Lifton | |
| D279,378 S | 6/1985 | Larsson | |
| 4,564,179 A * | 1/1986 | Hollingsworth | 269/71 |
| 4,645,156 A * | 2/1987 | Karapita | 248/280.11 |
| 4,657,217 A | 4/1987 | Kiesel et al. | |
| 4,826,432 A | 5/1989 | Roseiro | |
| 4,863,133 A * | 9/1989 | Bonnell | 248/280.11 |
| 4,901,967 A | 2/1990 | Petre | |
| 4,954,799 A | 9/1990 | Kumar | |
| 5,014,693 A | 5/1991 | Wright, II et al. | |

(Continued)

FOREIGN PATENT DOCUMENTS

CA   1225559   8/1987

(Continued)

OTHER PUBLICATIONS

English language Abstract for EP 0683016 A1 © 2002 Derwent Info Ltd.

(Continued)

*Primary Examiner*—Henry Bennett
*Assistant Examiner*—Nihir Patel
(74) *Attorney, Agent, or Firm*—Dority & Manning

(57) ABSTRACT

A support arm for use in a respiratory circuit is provided. The support arm includes a plurality of arm segments that are movably connected with one another such that the arm segments are adjustable with respect to another. At least one inflatable bladder is provided. The bladder is operably disposed at a point of connection between at least two of the arm segments. The arm segments are locked into position with respect to one another upon inflation of the bladder. The arm segments are released and positionable with respect to one another upon deflation of the bladder. Also, a respiratory support member is attached to one of the arm segments. The respiratory support member is configured for engaging the respiratory circuit to support the respiratory circuit.

28 Claims, 12 Drawing Sheets

U.S. PATENT DOCUMENTS

| | | | |
|---|---|---|---|
| 5,161,525 A | 11/1992 | Kimm et al. | |
| 5,170,790 A | 12/1992 | Lacoste et al. | |
| 5,184,365 A | 2/1993 | Stafford | |
| 5,231,981 A | 8/1993 | Schreiber et al. | |
| 5,263,478 A | 11/1993 | Davis | |
| 5,271,389 A | 12/1993 | Isaza et al. | |
| 5,301,921 A | 4/1994 | Kumar | |
| 5,319,540 A | 6/1994 | Isaza et al. | |
| 5,339,807 A | 8/1994 | Carter | |
| 5,368,019 A | 11/1994 | Latorraca | |
| 5,380,338 A | 1/1995 | Christian | |
| 5,390,666 A | 2/1995 | Kimm et al. | |
| 5,413,095 A | 5/1995 | Weaver | |
| 5,555,897 A | 9/1996 | Lathrop, Jr. et al. | |
| 5,692,494 A | 12/1997 | Pernetti et al. | |
| 5,704,900 A * | 1/1998 | Dobrovolny et al. | 600/229 |
| 5,772,174 A * | 6/1998 | Hirsch et al. | 248/447.1 |
| 5,779,209 A * | 7/1998 | Rello | 248/278.1 |
| 5,907,664 A * | 5/1999 | Wang et al. | 700/251 |
| 6,224,027 B1 | 5/2001 | Johnson et al. | |
| 6,499,851 B1 * | 12/2002 | Kelly et al. | 359/850 |
| 6,697,710 B1 * | 2/2004 | Wilcox | 700/245 |
| 2002/0195535 A1 * | 12/2002 | Carlson et al. | 248/575 |
| 2003/0086240 A1 | 5/2003 | Jobs et al. | |
| 2004/0228080 A1 * | 11/2004 | Hillman et al. | 361/683 |

FOREIGN PATENT DOCUMENTS

| | | |
|---|---|---|
| DE | 3703441 A1 | 8/1988 |
| DE | 9014848 U1 | 2/1991 |
| DE | 9321260 U1 | 5/1997 |
| EP | 0683016 A1 | 11/1995 |
| JP | 2000093414 | 4/2000 |
| WO | WO9927818 | 6/1999 |
| WO | WO0067690 | 11/2000 |
| WO | WO0156490 A1 | 8/2001 |

OTHER PUBLICATIONS

English language Abstract for JP 2000093414 A1 Japanese Patent Office.

* cited by examiner

RESPIRATORY CIRCUIT SUPPORT ARM

BACKGROUND

Ailments that affect the respiratory system can occur in people of any age group. These ailments can range anywhere from a temporary condition that requires minor treatment to a permanent disability that requires constant respiratory treatment.

Treatment of respiratory ailments may involve the use of various components configured in a respiratory circuit. For example, endotracheal intubation tubes are used primarily for the provision of an artificial airway in a patient's respiratory system for the passage of gasses and objects to and from the patient. Endotracheal tubes are typically rigid or semi-rigid cylindrical tubing that may extend from outside of the patient into the patient's lungs. Surgical instruments are then passed through this tubing into the patient's respiratory system in order to perform various medical procedures.

It may be the case that a patient's respiratory system is so severely impaired that a patient requires some or total assistance in breathing. Ventilators are commonly used to provide artificial respiration to patients in such circumstances. Ventilators are typically connected to a manifold of the breathing circuit to provide for artificial respiration of the patient. Ventilators may be configured so as to completely control the breathing of a patient, or configured such that the ventilator responds only when a patient has labored breathing to a predetermined extent.

Since a respiratory circuit has components located both on the inside and outside of a patient, the support and stability of a respiratory circuit is important in maintaining an optimal level of performance of the respiratory circuit and related components. It is sometimes the case that the tubing of a ventilator or even the tubing of a respiratory circuit is not rigid and needs to be supported. Also, it is often the case that a patient must be moved during the normal course of treatment, necessitating a change in position of the respiratory circuit. Additionally, even rigid or semi-rigid tubing in a respiratory circuit may need to be supported in order to provide for proper positioning of the tubing in relation to a patient or to provide for optimum patient comfort. In these circumstances, a support arm is sometimes used in order to support components of the respiratory circuit.

Typically, support arms have been located on a ventilator unit and extended therefrom in order to support tubing of the respiratory circuit. These support arms are typically provided with several joints that allow the support arm to enjoy a full range of motion. The tubing of the respiratory circuit is attached to one end of the support arm. This attachment may be a sliding support or a static connection. A caregiver may then manipulate the support arm such that the tubing is properly positioned. Support arms are typically provided with adjustment screws located at the various points of movement. A caregiver may manually tighten these adjustment screws in order to lock the support arm in the desired location. It is therefore the case that support arms typically require the caregiver to manually tighten and loosen from between two and four adjustment screws in order to properly manipulate and lock the support arm in the desired position. This adjustment requires the use of two hands by a caregiver.

The present invention is an improvement upon support arms that are used in supporting a respiratory circuit.

SUMMARY

Objects and advantages of the invention will be set forth in part in the following description, or may be obvious from the description, or may be learned through practice of the invention.

The present invention provides for a support arm for use in a respiratory circuit. The support arm includes a plurality of arm segments that are movably connected with one another such that the arm segments are adjustable with respect to one another. At least one inflatable bladder is provided that is operably disposed at a point of connection between at least two of the arm segments. Inflation of the bladder causes the arm segments to be locked into position with respect to one another. Deflation of the bladder causes the arm segments to be released and therefore positionable with respect to one another. Also included is a respiratory support member that is attached to one of the arm segments. The respiratory support member is configured for engaging and support a component of the respiratory circuit.

Also provided in the present invention is a support arm as previously discussed where at least one of the arm segments may have a flexible section. Also, a least one of the inflatable bladders is located in the flexible section of the arm segment. The bladder is inflatable to rigidify the flexible section.

Further provided in the present invention is an embodiment of a support arm as previously discussed where the bladder is configured at a point of connection between all of the arm segments.

Also provided for in the present invention is an embodiment of a support member as previously discussed where the bladder is within at least one of the arm segments.

The present invention also includes an embodiment of a support arm for use with a respiratory circuit that has a plurality of arm segments. At least one of the arm segments is a rigid member, and at least one of the arm segments has a flexible section. The arm segments are connected to one another by swivel joints to allow the arm segments to swivel with respect to one another. A bladder is located inside of the arm segments. The bladder may be continuous through the arm segments. The bladder is inflatable in order to effect a locking of the arm segments with respect to one another. A respiratory support member is also provided and may be attached to one of the arm segments and is adjustable with respect to the arm segment. Inflation of the bladder causes a locking of the respiratory support member and prevents adjustment of the respiratory support member with respect to the arm segment. The respiratory support member is configured for engaging a component of the respiratory circuit.

In one particular embodiment, the present invention further provides for a support arm as immediately discussed where the support arm has three arm segments. Two of the arm segments are rigid and one of the arm segments has a flexible section. The respiratory support member is attached to the arm segment having a flexible section.

Additionally, the present invention includes a support arm for use with a respiratory circuit as previously discussed where one of the arm segments may have a control member attached thereto. The control member is located proximate to the respiratory support member. Activation of the control member causes deflation of the bladder and unlocking of the arm segments to allow a user to manipulate the arm segments.

Further provided for under the present invention is a support arm for use with a respiratory circuit as previously discussed where an embodiment of the respiratory support member has a ball and socket connection. This connection is used for effecting adjustment of the respiratory support member in relation to the arm segment.

In one particular multi-arm embodiment of the invention, the support arm has three segments. Two of the arm segments are a rigid member, and the other has a flexible section. One of the rigid arm segments is adjustably connected on one end to a ventilator. The two rigid arm segments are adjustably connected to one another by a first swivel joint. One of the rigid arm segments and the arm segment having the flexible section are adjustably connected to one another by a second swivel joint. The flexible section is formed by a corrugated member. Further, a respiratory support member is connected to the arm segment that has the flexible section. The respiratory support member has one end configured for engagement with a tube of a respiratory circuit to support the tube. The respiratory support member has a pivot connection to allow for adjustment of the respiratory support member. Also, a flexible bladder is present. The bladder is disposed through the arm segments. Inflation of the bladder effects a locking of the swivel joints and the flexible section to cause a locking of the arm segments and prevent relative motion between the arm segments. Inflation of the bladder effects a locking of the pivot connection of the respiratory support member to prevent adjustment of the respiratory support member.

BRIEF DESCRIPTION OF THE DRAWINGS

An embodiment of the present invention is described by way of example with reference to the accompanying drawings, in which.

DETAILED DESCRIPTION

Figure 1:
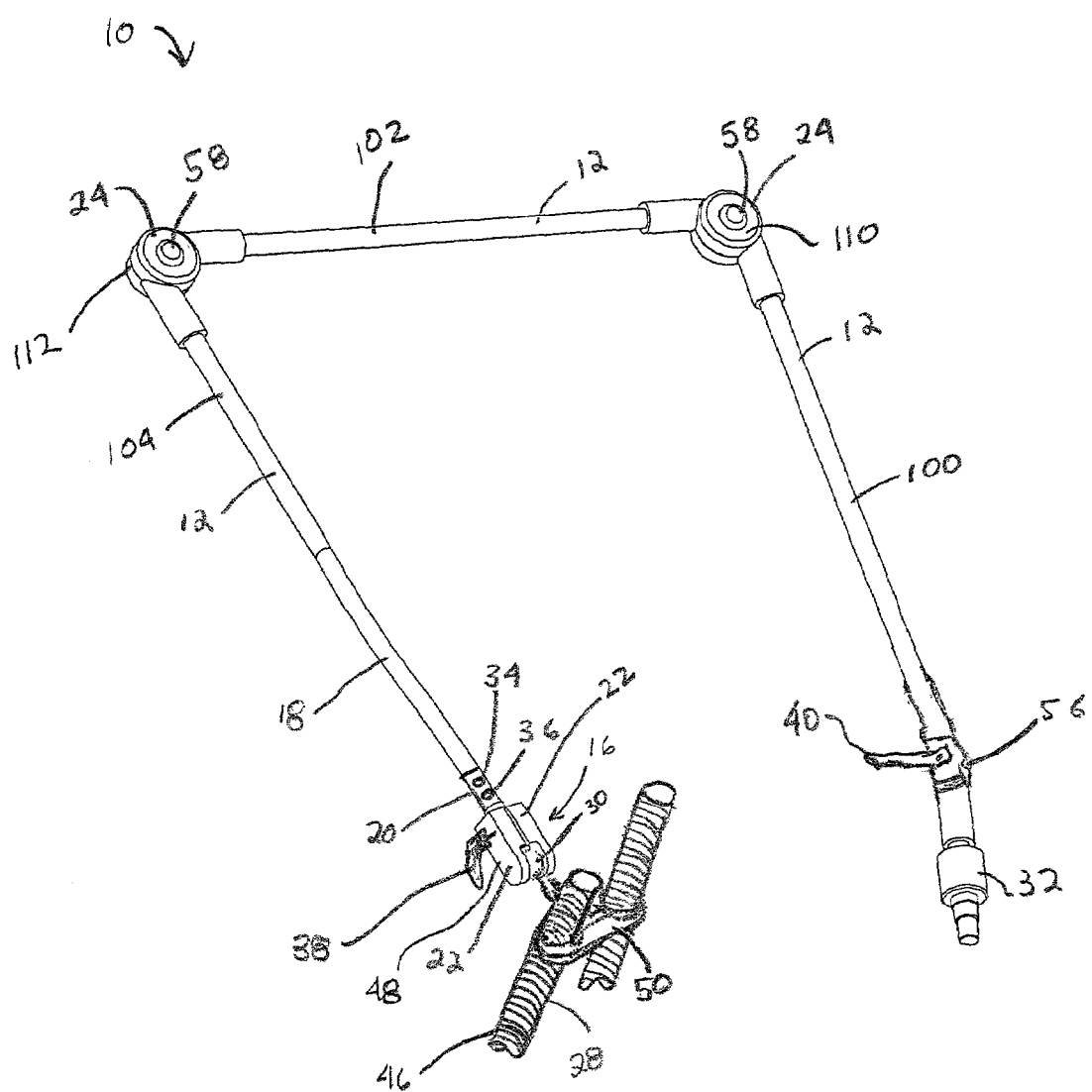
FIG. 1 is a perspective view of an exemplary embodiment of a support arm of the present invention. The support arm is shown supporting a component of a respiratory circuit.

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

An exemplary embodiment of a support arm 10 in accordance with the present invention is shown in FIG. 1. The support arm 10 is designed to be attached to a ventilator (not shown). However, it is to be understood that the support arm 10 may in other exemplary embodiments be attached to objects other than a ventilator. The support arm 10 is configured to hold a respiratory circuit component 28. In order to properly position the support arm 10 such that it may support the respiratory circuit component 28, the support arm 10 is constructed of a series of arm segments 12. Although shown as having three arm segments 12 in FIG. 1, it is to be understood that the support arm 10 may be constructed of any number of arm segments 12. The arm segments 12 are designed to be movable with respect to one another such that the support arm 10 can be articulated and moved into any desired position. In order to permit relative movement between the arm segments 12, any manner of suitable swivel joints 24 are provided that connect the arm segments.

A first arm segment 100 is present and is connected on one end to a ventilator connection adjustment 56. The ventilator connection adjustment 56 is provided with a ventilator connection adjustment handle 40. The ventilator connection adjustment handle 40 may be loosened to in order to allow for adjustment of the first arm segment 100 with respect to a ventilator connection member 32. In one exemplary embodiment of the present invention, the ventilator connection member 32 is connected to a ventilator. The ventilator connection adjustment 56 may therefore allow the first arm segment 100 to move vertically, horizontally, or rotationally with respect to the ventilator connection member 32. The other end of the first arm segment 100 is connected to a first swivel joint 110 which is also connected to an end of a second arm segment 102. A point of connection 58 is defined between the first arm segment 100 and the second arm segment 102. The first swivel joint 110 allows for relative rotational movement between the first arm segment 100 and the second arm segment 102. In the exemplary embodiment shown in FIG. 1, the first arm segment 100 and second arm segment 102 are both rigid members.

The second arm segment 102 is likewise connected to a second swivel joint 112 that is also connected to a third arm segment 104. The second swivel joint 112 allows for relative rotational movement between the second arm segment 102 and the third arm segment 104. The second arm segment 102 and the third arm segment 104 define a point of connection 58.

The third arm segment 104 has a flexible section 18 that runs along a part of the length of the third arm segment 104. The flexible section 18 allows for the third arm segment 104 to be more precisely adjusted during the adjustment of the support arm 10. The flexible section 18 is connected on one end thereof to a respiratory support member 16. The respiratory support member 16 is connected to a respiratory circuit gripping member 50. The respiratory circuit gripping member 50 engages a tube 46 of the respiratory circuit 28 and positions and supports the tube 46 in the proper location.

One advantage of a particular embodiment of the present invention resides in having a user adjust the support arm 10 to a desired position using only one hand. Once placed in the proper position for the support of a respiratory circuit 28, the user may then use a control member 20 to lock the support arm 10 into the desired position. The control member 20 is located on the third arm segment 104. However, it is to be understood that in other exemplary embodiments of the present invention, the control member 20 may be placed on locations other than the arm segments 12. However, locating the control member 20 on the third arm segment 104 and proximate to the respiratory support member 16 allows for the user to activate the control member 20 without having to move his or her hand off of the respiratory support member 16. In other words, the user may position and lock the support arm 10 by the use of only one hand.

The control member 20 is equipped with an inflation button 34 and a deflation button 36. The inflation button 34 and deflation button 36 are used to control the inflation and deflation of a bladder 14 that is not shown in FIG. 1, but which runs through the swivel joints 24, the flexible section 18, and the arm segments 12. As will be explained in greater detail below, inflation of the bladder 14 causes the swivel joints 24 and the flexible section 18 to lock in their present position and prevents the support arm 10 from moving. Deflation of the bladder 14 causes these members to again become movable and flexible. Therefore, the support arm 10 of the present invention uses a bladder 14 to control the locking and unlocking of the support arm 10.

Figures 4, 5:
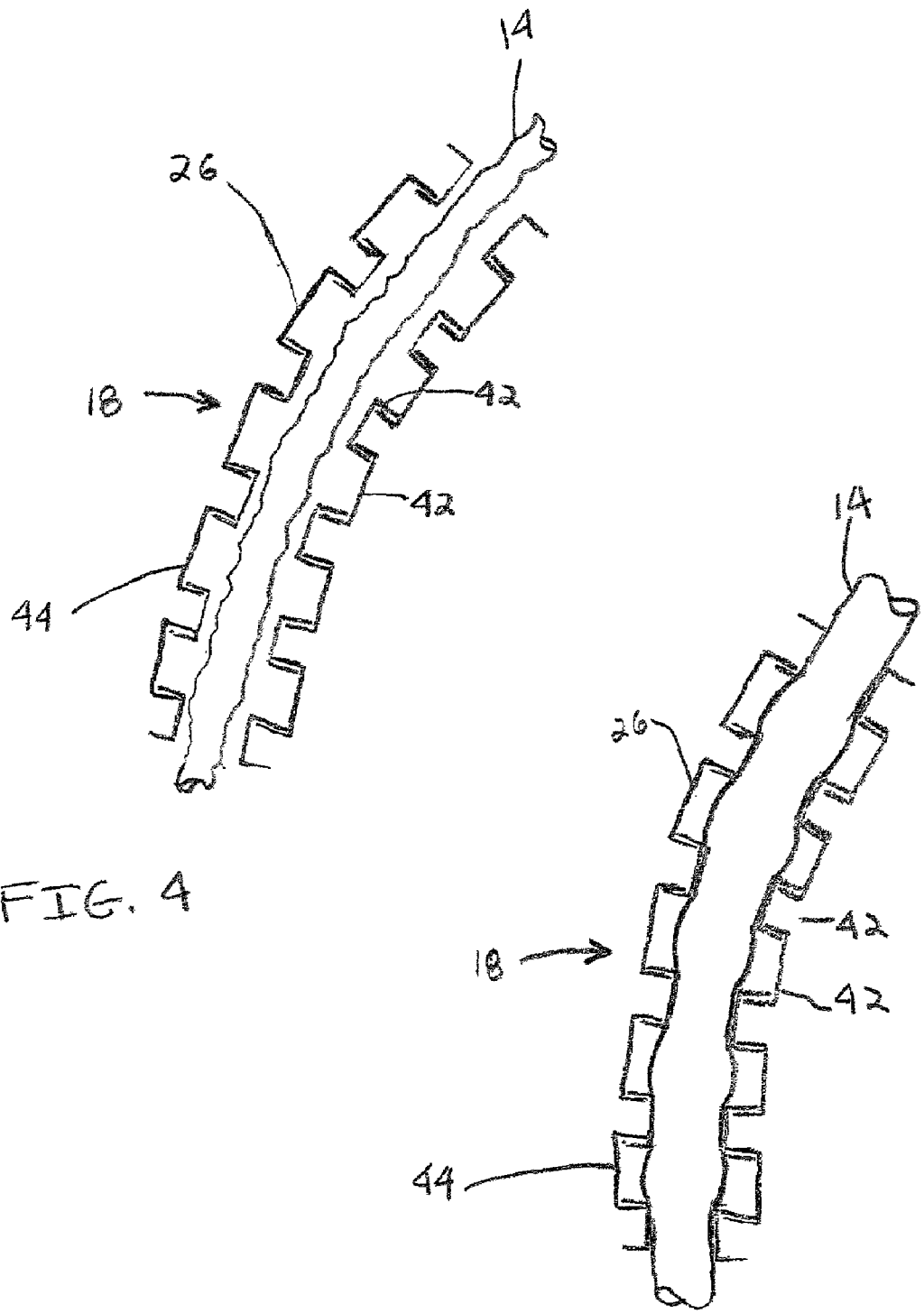
FIG. 4 is a partial cross-sectional view of an exemplary embodiment of a flexible section in accordance with the present invention. The flexible section is free to move, and an uninflated bladder runs therethrough.
FIG. 5 is a view of the flexible section shown in FIG. 4 with the bladder inflated. Once inflated, the flexible section is fixed and prevented from moving.

FIG. 4 shows an exemplary embodiment of a section of the flexible section 18 in accordance with the present invention. Here, the flexible section 18 is a corrugated member 44 that is composed of corrugated tube 26 which has a series of C-shaped interconnected members 42. The interconnection of the C-shaped interconnected members 42 allows for the corrugated tube 26 to be flexible and moveable to a desired position. The bladder 14 is shown in an uninflated state running through the interior of the corrugated tube 26.

FIG. 5 shows the flexible section 18 as in FIG. 4, however, the bladder 14 is shown in an inflated state. Once inflated, the bladder 14 pushes against the C-shaped interconnected members 42 and urges them against one another. This urging locks the C-shaped interconnected members 42 against one another and prevents movement of the corrugated tube 26. Therefore, FIG. 5 shows the flexible section 18 in a locked configuration.

Figure 2:
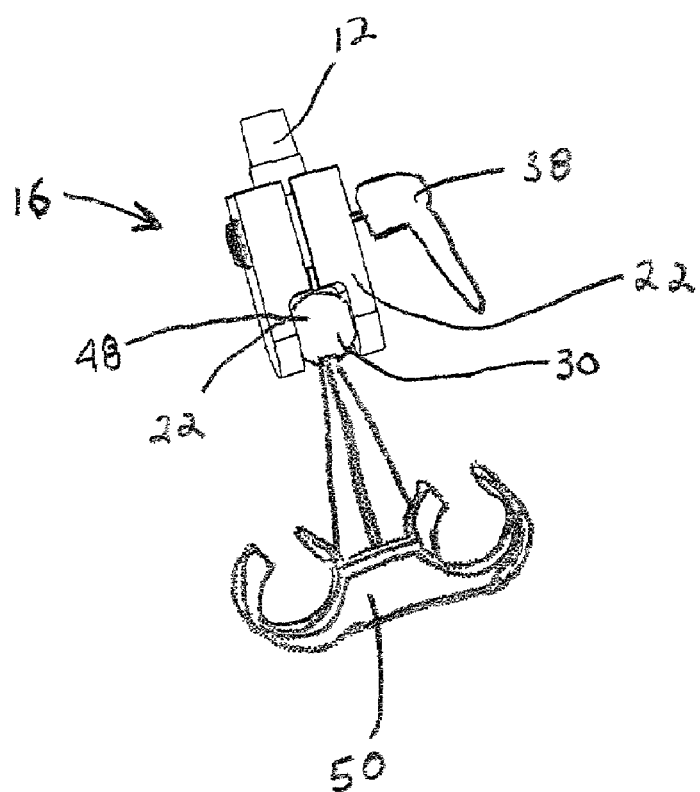
FIG. 2 is a perspective view of an exemplary embodiment of a respiratory support member of the present invention. The respiratory support member has a respiratory support adjustment handle attached thereon.
Figure 3:
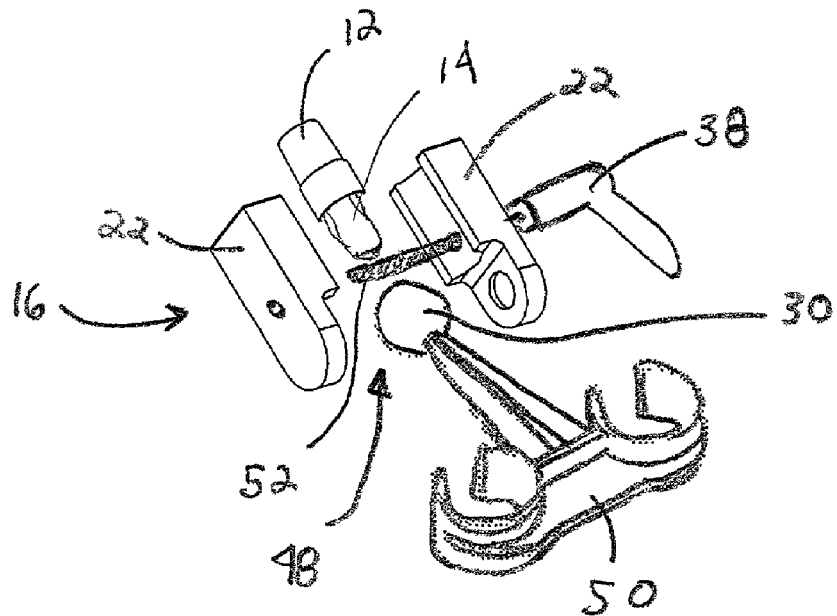
FIG. 3 is an exploded perspective view of the respiratory support member shown in FIG. 2.

FIG. 2 shows an exemplary embodiment of a respiratory support member 16 in accordance with the present invention. The respiratory support member 16 includes two sections 22 movably connected to one another by a screw 52, as shown in FIG. 3, and a respiratory support adjustment handle 38. A pivot connection 48 is shown being formed by a ball and socket connection 30. This connection allows for the adjustment of the respiratory circuit gripping member 50. The respiratory support adjustment handle 38 may be loosened such that the respiratory circuit gripping member 50 is removable from the respiratory support member 16. Additionally, the respiratory support adjustment handle 38 may be tightened so that the ball and socket connection 30 is engaged and prevented from allowing the respiratory circuit gripping member 50 to move. Further, as shown in FIG. 3, the bladder 14 may extend into the respiratory support member 16. When inflated, the bladder 14 is urged against both sections 22 of the respiratory support member 16. This causes the two sections 22 to pivot and firmly engage the ball and socket connection 30 and prevent the respiratory circuit gripping member 50 from moving. Therefore, the locking of the respiratory circuit gripping member 50 into place may be accomplished through the use of a first adjustment by the respiratory support adjustment handle 38, and then further securely locked into place via inflation of the bladder 14.

Figure 10:
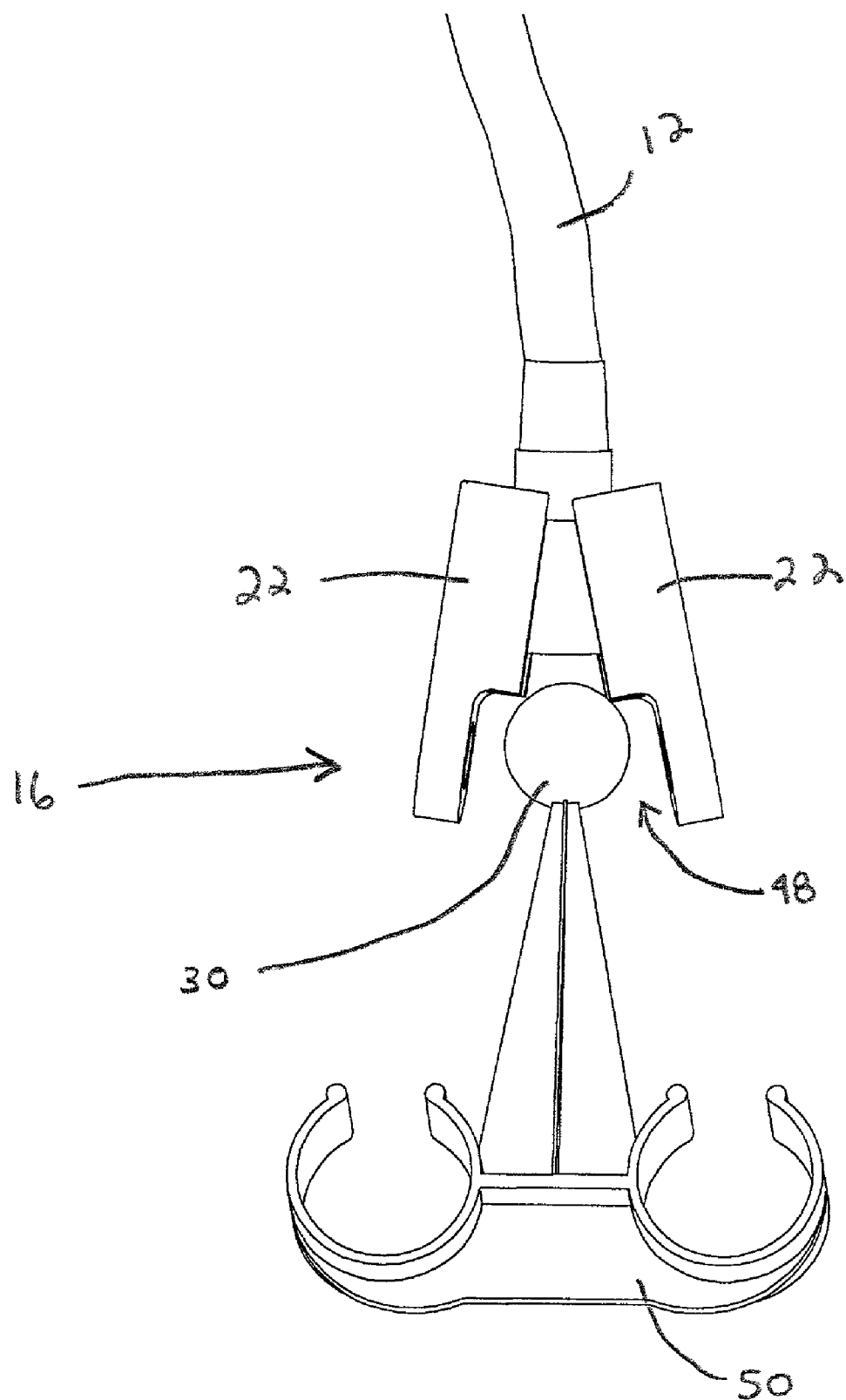
FIG. 10 is a perspective view of an exemplary embodiment of a respiratory support member in accordance with the present invention. The view shows the respiratory support member having a ball and socket connection in a disengaged state.
Figure 11:
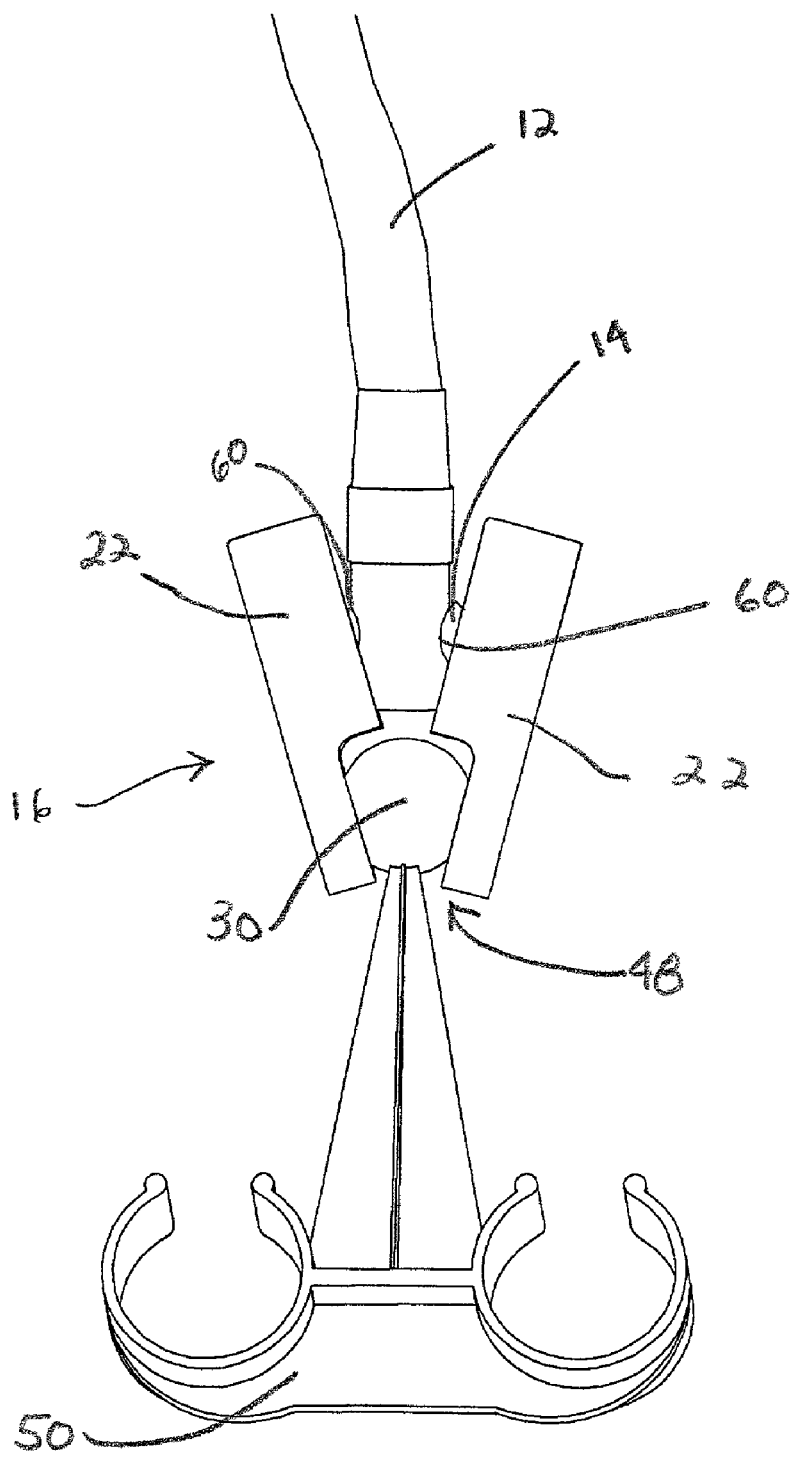
FIG. 11 is a perspective view of the respiratory support member shown in FIG. 10. The drawing shows a bladder acting on sections of the respiratory support member to engage the ball and socket connection and hold the respiratory circuit gripping member.

FIGS. 10 and 11 more particularly demonstrate the locking of the ball and socket connection 30. FIG. 10 shows an exemplary embodiment of the respiratory support member 16 in accordance with the present invention. Here as shown for clarity, the two sections 22 of the respiratory support member 16 do not engage the ball of the ball and socket connection 30. In one exemplary embodiment of the present invention, the sections 22 loosely engage the ball of the ball and socket connection 30 even before inflation of the bladder 14. The pivot connection 48 is thus loosely engaged and the respiratory circuit gripping member 50 is free to move. FIG. 11 shows the respiratory support member 16 of FIG. 10 where the pivot connection 48 is engaged and prevented from moving. Here, the arm segment 12 is provided with two apertures 60. The bladder 14 is present within the arm segment 12, and inflation thereof forces the bladder 14 to move out of the apertures 60. The inflated bladder 14 then contacts both of the sections 22 of the respiratory support member 16 and pivots the two sections onto the ball of the ball and socket connection 30. This creates a locking force on the ball and socket connection 30 and hence results in a locking of the respiratory circuit gripping member 50.

Figure 14:
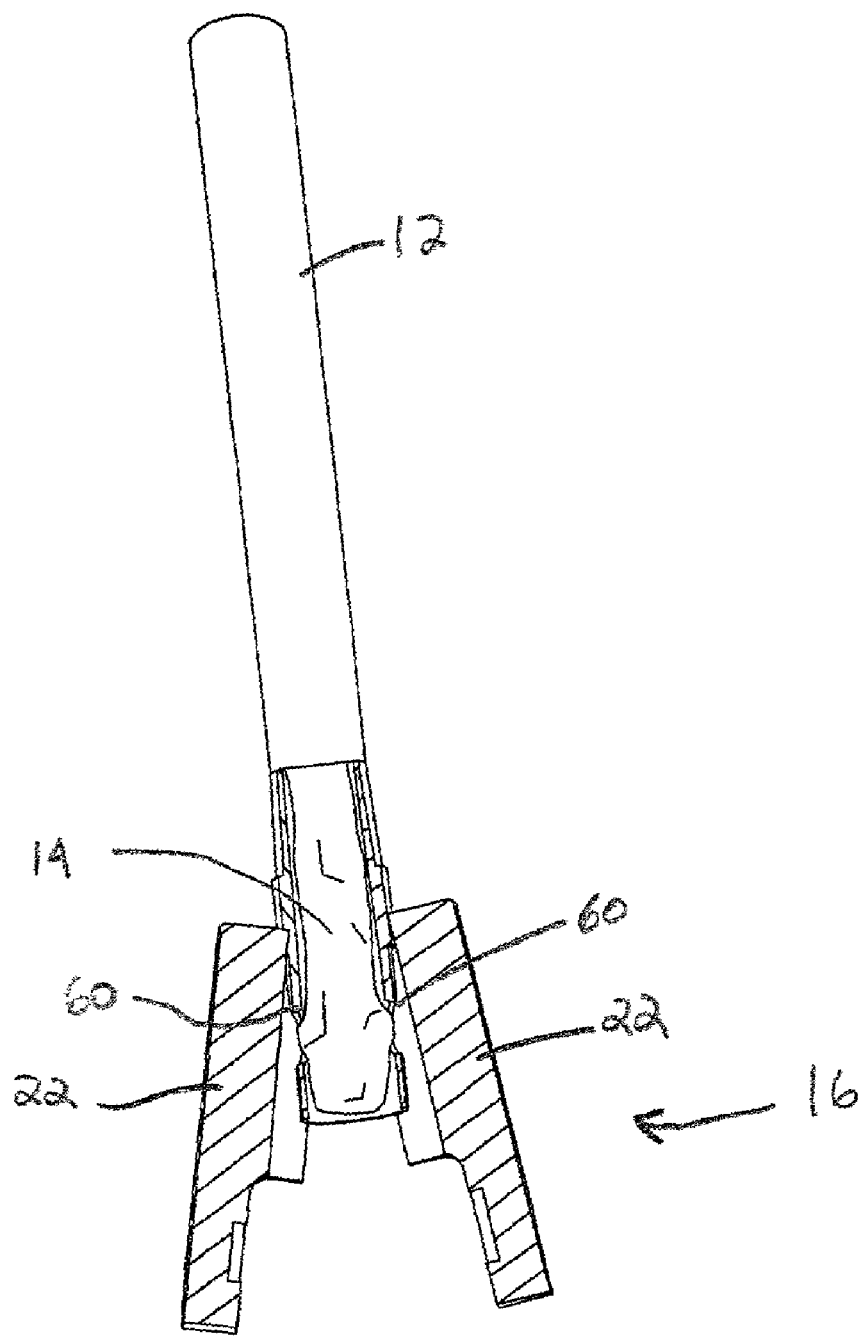
FIG. 14 is a partial cross-sectional view of an embodiment of a respiratory support member in accordance with the present invention. A bladder is shown in an uninflated state, and two sections of the respiratory support member are not engaged.
Figure 15:
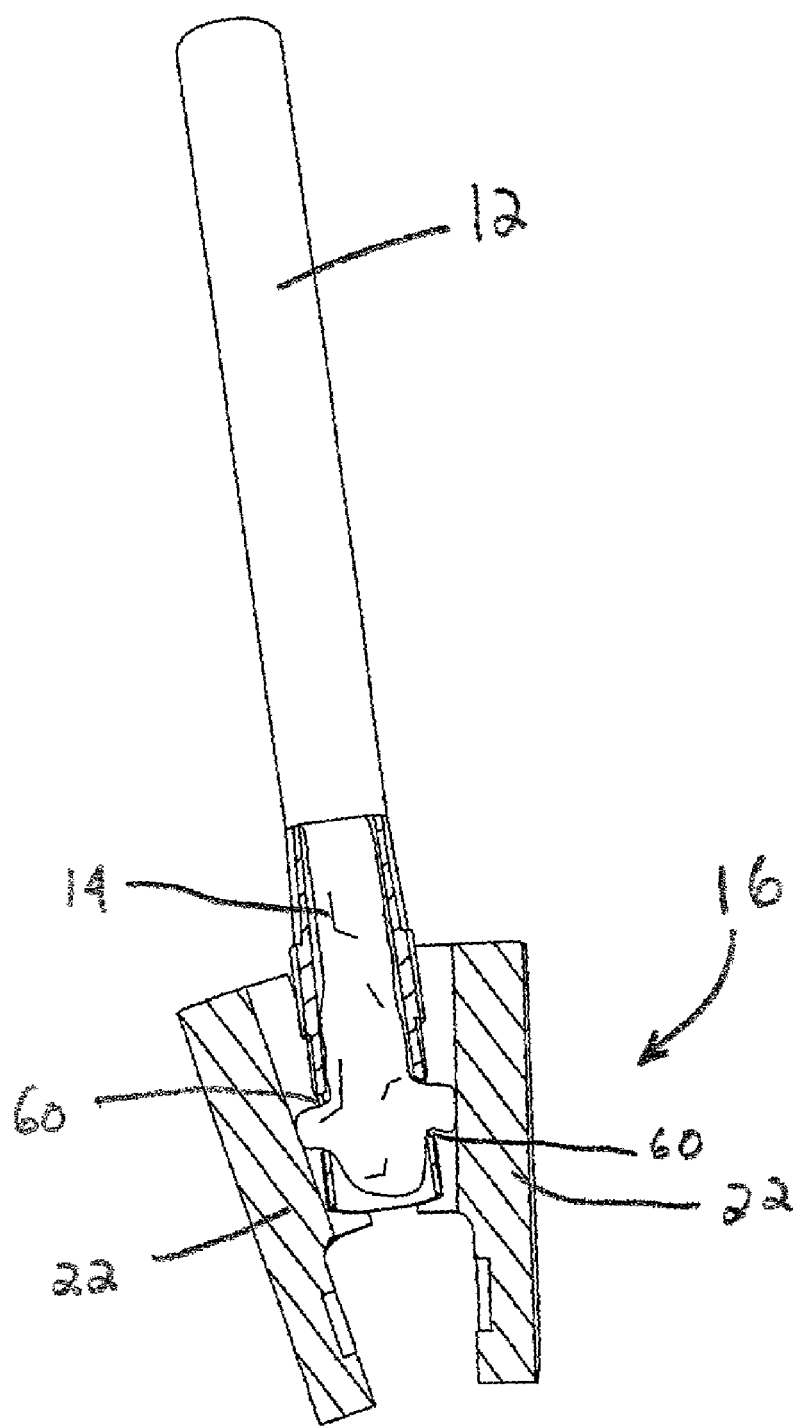
FIG. 15 is a partial cross-sectional view of the exemplary embodiment of the respiratory support member shown in FIG. 14. The bladder is shown in an inflated state engaging the two sections of the respiratory support member.

Again, this locking action by the bladder 14 is shown in greater detail in FIGS. 14 and 15. FIG. 14 shows the bladder 14 in an uninflated state and the sections 22 of the respiratory support member 16 in an unlocked configuration. FIG. 15 shows the bladder 14 in an inflated state and extending through the apertures 60 to engage the two sections 22 of the respiratory support member 16. Here, the two sections 22 of the respiratory support member 16 are now in a locked configuration.

Figure 6:
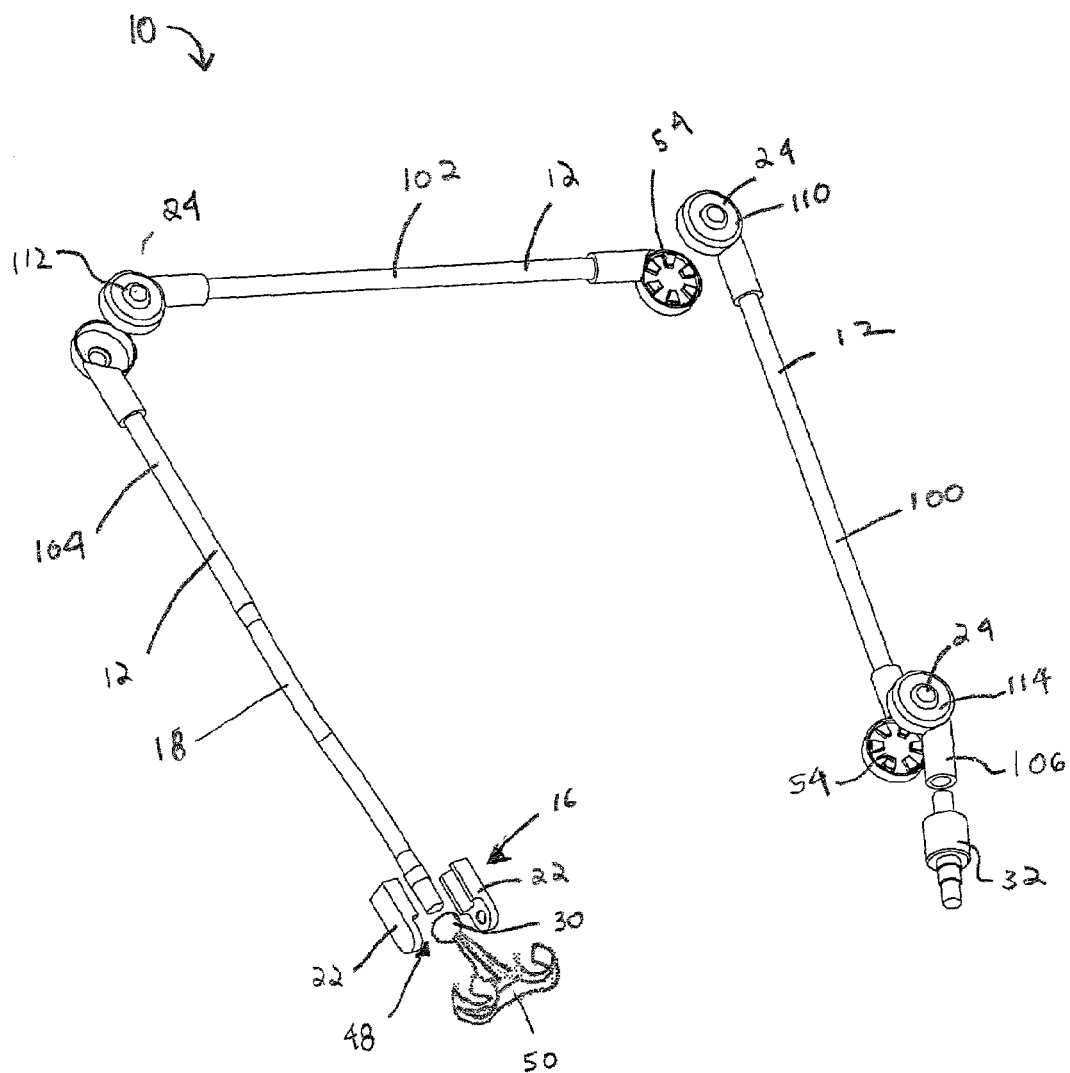
FIG. 6 is an exploded assembly view of an exemplary embodiment of a support arm in accordance with the present invention. The drawing shows the swivel joints that connect the support arms.

FIG. 6 shows another exemplary embodiment of a support arm 10 in accordance with the present invention. Here, a third swivel joint 114 is present and is connected to the first arm segment 100. Also connected to the third swivel joint 114 is a fourth arm segment 106. The third swivel joint 114 allows for relative movement between the first arm segment 100 and the fourth arm segment 106. The fourth arm segment 106 is also connected to the ventilator connection member 32. Therefore, it is to be understood that the present invention includes various exemplary embodiments that consist of any number of swivel joints 24 and arm segments 12. Also, various exemplary embodiments of the present invention exist where the ventilator connection adjustment 56 and the ventilator connection adjustment handle 40 are not present to allow for the adjustment of the arm segments 12. Additionally, FIG. 6 discloses an exemplary embodiment of the support arm 10 that does not have a respiratory support adjustment handle 38 that is used to adjust the respiratory support member 16.

Figure 9:
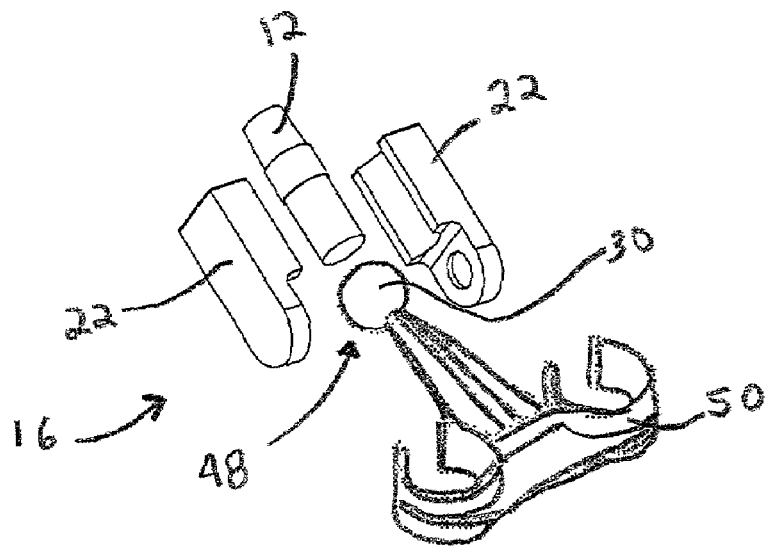
FIG. 9 is an exploded assembly view of the embodiment of the respiratory support member shown in FIG. 8.
Figure 8:
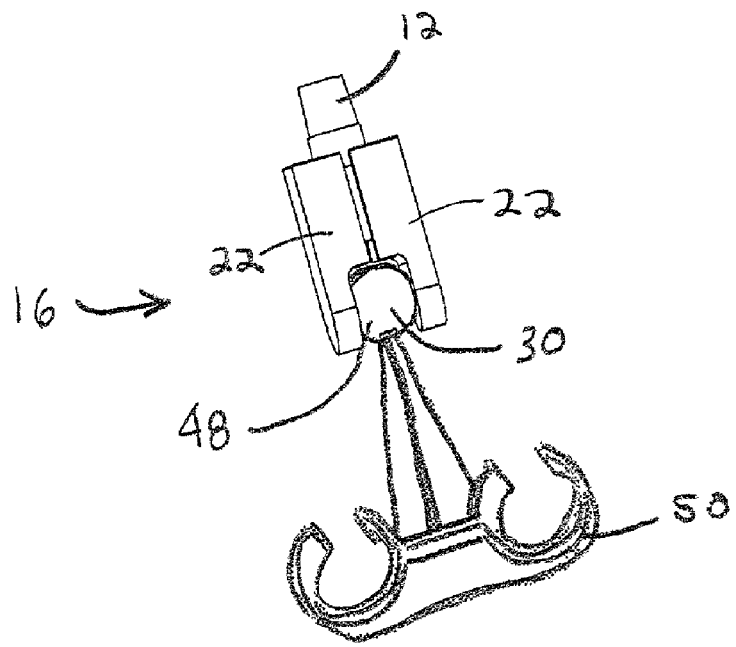
FIG. 8 is a perspective view of an exemplary embodiment of a respiratory support member in accordance with the present invention.

A respiratory support member 16 that does not have the respiratory support adjustment handle 38 is shown in more detail in FIG. 8. Here, the pivot connection 48 may be formed by simply having a frictional engagement of the ball and socket connection 30. Additionally, as shown in FIG. 9, the two sections 22 of the respiratory support member 16 do not have to be engaged by a bladder 14. Here, the two sections 22 are adhered to one another by commonly known techniques such as adhesion or sonic welding. As can be seen, the respiratory support member 16 can be a purely mechanical connection and does not need to have a bladder 14 for its proper operation in other exemplary embodiments of the present invention.

Figure 7:
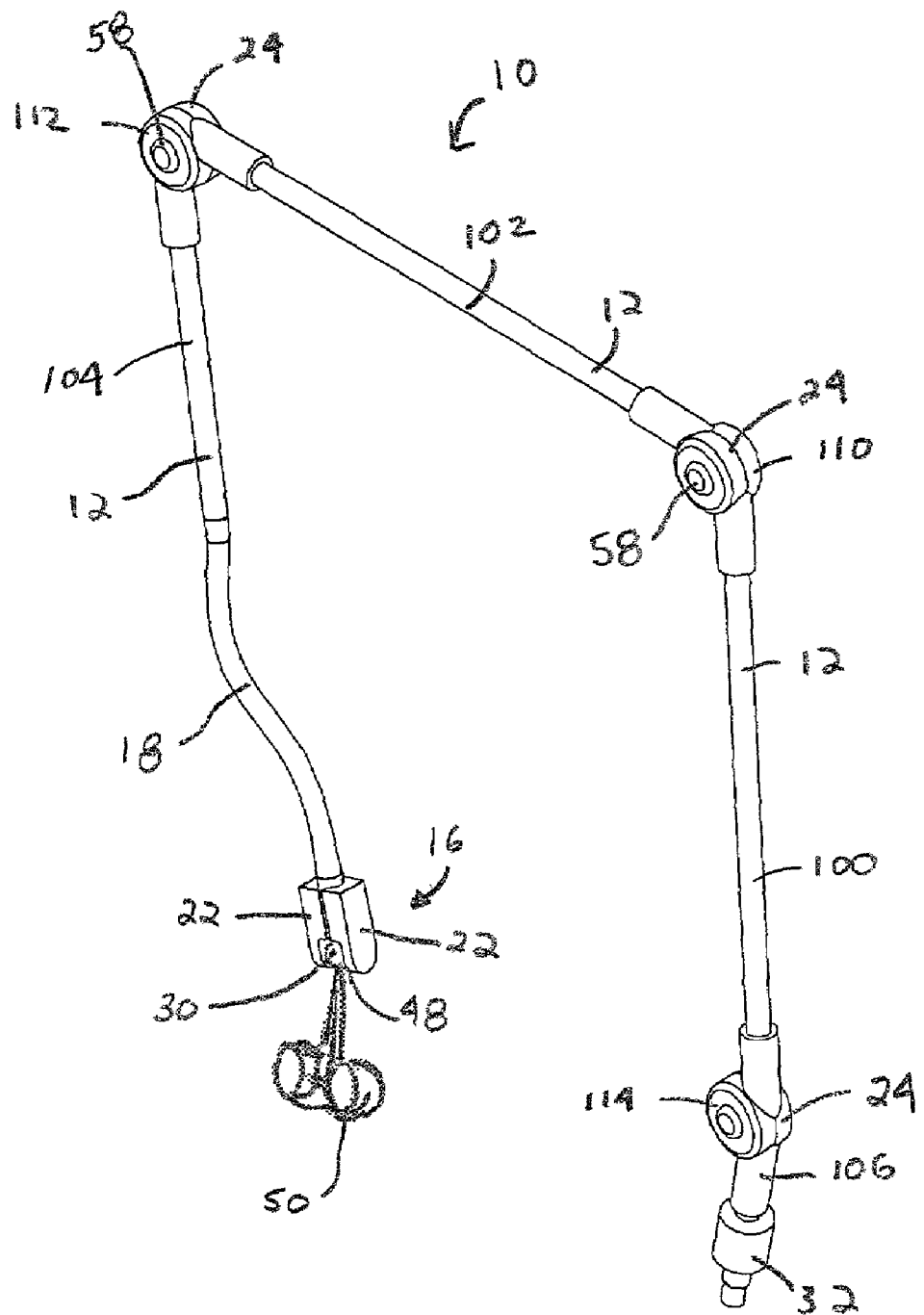
FIG. 7 is an assembled perspective view of the exemplary embodiment shown in FIG. 6.

FIG. 7 shows this type of respiratory support member 16 being used on a support arm 10 in another exemplary embodiment of the present invention. The support arm 10 shown in FIG. 7 is the assembled support arm 10 of FIG. 6. Here, inflation of the bladder 14 will only effect a locking of the swivel joints 24 and the flexible section 18, and not the locking of the respiratory support member 16. It is to be understood that in other exemplary embodiments of the present invention, the third arm segment 104 does not need to have a flexible section 18 included thereon. As such, other exemplary embodiments of the present invention may include a third arm segment 104 that is completely rigid. In addition, the flexible section 18 does not have to be a corrugated tube 26, but may be made flexible via other means commonly known in the art.

Figure 12:
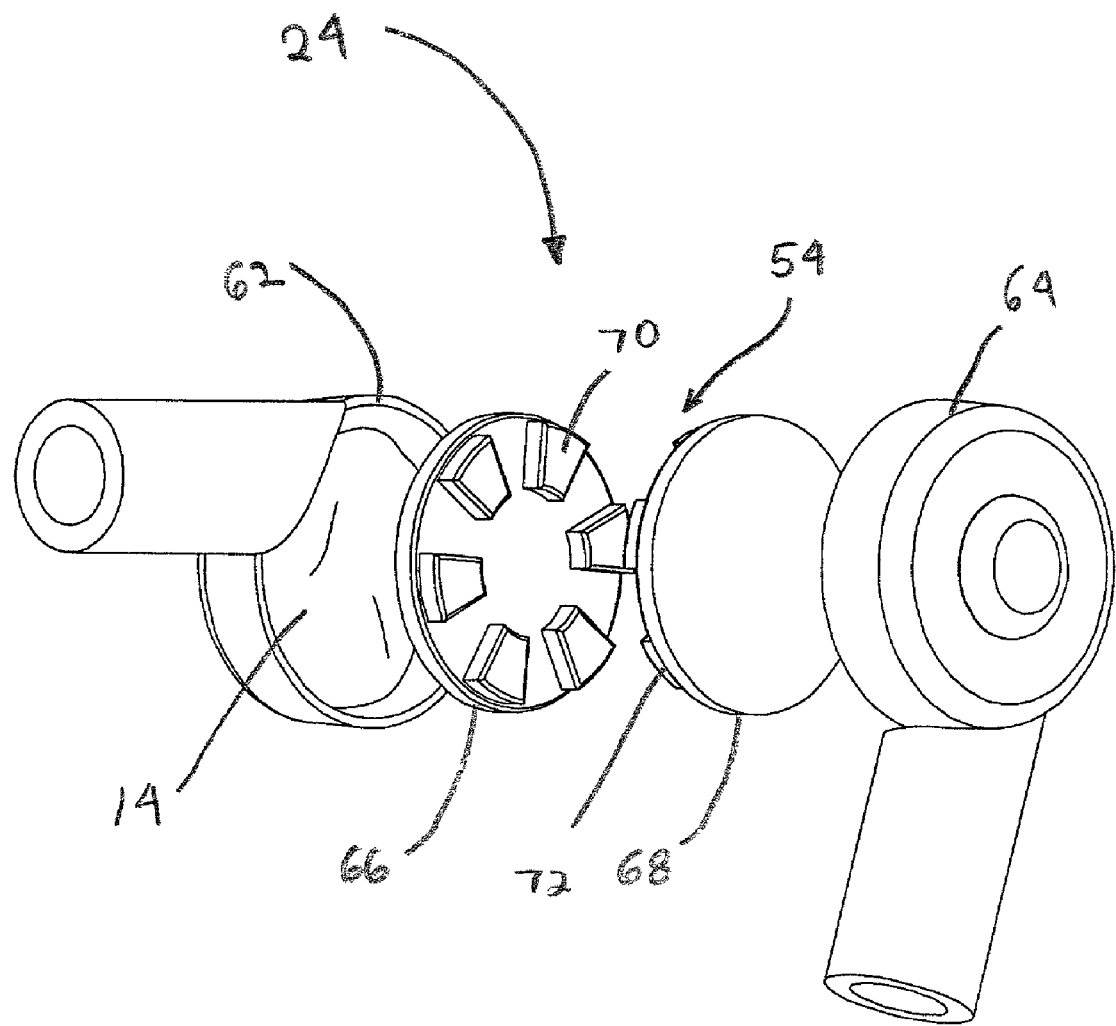
FIG. 12 is an exploded assembly view of an exemplary embodiment of a swivel joint in accordance with the present invention. The drawing shows a bladder disposed within swivel cups and configured to engage a snap ring configuration.

FIG. 12 shows an exploded view of the swivel joint 24 in accordance with the present invention. Here, the swivel joint 24 has a snap ring configuration 54 that includes a first snap ring 66 and a second snap ring 68. The first snap ring 66 is configured to be disposed within a first swivel cup 62, and the second snap ring 68 is configured to be disposed within a second swivel cup 64. The bladder 14 is disposed within the first swivel cup 62 and also within the second swivel cup 64, although this cannot be seen in FIG. 12. While the bladder 14 is in an uninflated state, the first and second snap rings 66 and 68 do not engage one another and are free to rotate with respect to one another. In effect, the swivel joint 24 is free to swivel when the bladder 14 is uninflated.

The first snap ring 66 is provided with a series of first snap ring projections 70, and the second snap ring 68 is provided with a series of second snap ring projections 72. During inflation of the bladder 14, the first and second snap rings 66 and 68 are urged against one another. The configurations of the first and second snap ring projections 70 and 72 are designed such that they intermesh with one another when the first and second snap rings 66 and 68 are urged against one another. This intermeshing causes a locking force between the first and second snap rings 66 and 68. This locking force therefore prevents the swivel joint 24 from swiveling and hence locks the arm segments 12 in place.

Figure 13:
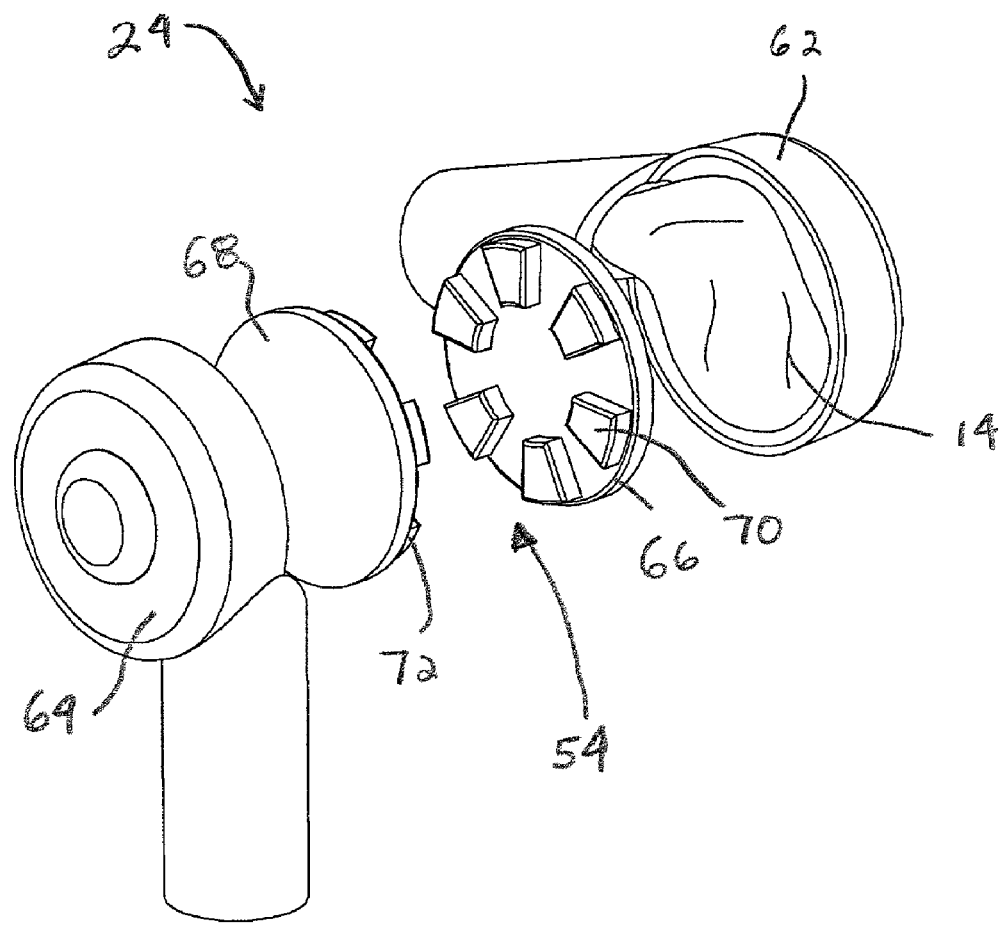
FIG. 13 is an exploded assembly view of the swivel joint shown in FIG. 12. The drawing shows the swivel joint at a different angle than that shown in FIG. 12.

FIG. 13 shows the swivel joint 24 of FIG. 12 from a different angle. Although described as having the bladder disposed within each of the first and second swivel cups 62 and 64, other exemplary embodiments of the present invention include a swivel joint 24 that has the bladder 14 disposed within only one of the swivel cups 62 or 64. In addition, other exemplary embodiments of the present invention may include a configuration of the swivel joint 24 where the bladder 14 is continuous through the swivel joint 24. In such an exemplary embodiment, the bladder 14 may for instance pass through the center of both the first and second snap rings 66 and 68. Additionally, other configurations of the swivel joint 24 are possible where the swivel joint 24 is locked in place due to the inflation of the bladder 14. The exemplary embodiment shown in FIGS. 12 and 13 is only one such configuration, and others are conceivable within the present invention.

Other exemplary embodiments of the present invention may include a configuration where the bladder 14 is continuous throughout all of the arm segments 12, the swivel joints 24, the flexible section 18, and into the respiratory support member 16. Additionally, other exemplary embodiments may include configurations where the bladder 14 is present within the swivel joints 24, the flexible section 18, and the respiratory support member 16 and is connected to all of these sections via tubes through arm segments 12. In essence, exemplary embodiments of the present invention may include a bladder 14 that is either one or several pieces. Another exemplary embodiment of the present invention exists where the bladder 14 is outside of the arm segments 12 and wraps around the swivel joints 24 to lock them in place. The pressure used to inflate the bladder 14 may be provided by the ventilator through the ventilator connection member 32. In one particular exemplary embodiment of the present invention, the gas source used to inflate the bladder 14 is provided by the compressor in the ventilator. However, it is to be understood that other gas sources may be utilized in order to inflate the bladder 14. The bladder 14 allows for the user to manipulate and then lock the support arm 10 into place without having to manually tighten the swivel joints 24. Such an arrangement is provided when single handed operation of the support arm 10 is desired.

It should be understood that the present invention includes various modifications that can be made to the exemplary embodiments of the respiratory circuit support arm described herein as come within the scope of the appended claims and their equivalents.

What is claimed is:

1. A support arm for use in a respiratory circuit, comprising:
   a plurality of arm segments movably connected with one another such that said arm segments are adjustable with respect to one another;
   at least one inflatable bladder operably disposed at a point of connection between at least two of said arm segments, wherein upon inflation of said bladder said arm segments are locked into position with respect to one another and upon deflation said arm segments are released and positionable with respect to one another; and
   a respiratory support member attached to one of said arm segments, said respiratory support member configured for engaging a component of the respiratory circuit to support the respiratory circuit.

2. The support arm of claim 1, wherein said bladder is configured at a point of connection between all of said arm segments.

3. The support arm of claim 2, wherein said bladder is a tube that extends through all of said arm segments.

4. The support arm of claim 1, wherein said bladder is within at least one of said arm segments.

5. The support arm of claim 4, wherein said bladder traverses the point of connection between all of said arm segments.

6. The support arm of claim 1, wherein:
at least one of said arm segments has a flexible section; and
further comprising at least one said inflatable bladder located in said flexible section of said arm segment and is inflatable to rigidify said flexible section.

7. The support arm of claim 1, wherein at least one of said arm segments is configured so as to be adjustably mounted to a ventilator unit.

8. The support arm of claim 1, wherein said bladder is inflated and deflated by activation of at least one control member, said at least one control member located on said arm segment and proximate to said respiratory support member.

9. The support arm of claim 1, wherein the inflation of said bladder hinders the adjustment between all of said arm segments, deflation of said bladder permits adjustment between all of said arm segments.

10. The support arm of claim 1, wherein said arm segments are adjustable and said bladder is configured to be inflatable and deflatable by a user employing only one hand.

11. The support arm of claim 1, wherein only one bladder is present.

12. The support arm of claim 1, wherein said respiratory support member has at least two sections being movable with respect to one another, wherein inflation of said bladder urges against one of said sections and causes both of said sections to be fixed with respect on one another.

13. The support arm of claim 6, wherein:
said arm segments are three in number and are movably connected with one another by swivel joints; and
said flexible section of said arm segment is a corrugated tube.

14. The support arm of claim 6, wherein:
said arm segments are four in number and are movably connected with one another by swivel joints; and
said flexible section of said arm segment is a corrugated tube.

15. The support arm of claim 1, wherein said arm segments are movably connected with one another by swivel joints, said swivel joints having a snap ring configuration, said snap ring configuration is disengaged during deflation of said bladder and allows said swivel joint to move freely, inflation of said bladder engages said snap ring configuration and locks said swivel joint.

16. A support arm for use with a respiratory circuit having a ventilator, comprising:
a plurality of arm segments, at least one of said arm segments being a rigid member and at least one of said arm segments having a flexible section, said arm segments being connected to one another by swivel joints to allow said arm segments to swivel with respect to one another;
a bladder located inside of said arm segments, said bladder being continuous through said arm segments, said bladder being inflatable to effect a locking of said arm segments with respect to one another;
a respiratory support member attached to one of said arm segments and adjustable with respect to said arm segment, wherein inflation of said bladder causes a locking of said respiratory support member preventing adjustment of said respiratory support member with respect to said arm segment, said respiratory support member configured for engagement with a respiratory circuit.

17. The support arm for use with a respiratory circuit of claim 16, wherein said support arm has three arm segments, two of said arm segments are rigid and one of said arm segments has a flexible section, said respiratory support member being attached to said arm segment having a flexible section.

18. The support arm for use with a respiratory circuit of claim 16, wherein one of said arm segments has a control member attached thereon, said control member is located proximate to said respiratory support member, activation of said control member causes deflation of said bladder and unlocking of said arm segments to allow a user to manipulate said arm segments.

19. The support arm for use with a respiratory circuit of claim 16, wherein said respiratory support member has a ball and socket connection for effecting adjustment of said respiratory support member in relation to said arm segment.

20. The support arm for use with a respiratory circuit of claim 16, wherein one of said arm segments is configured so as to be adjustably connected to a ventilator, and said bladder is inflated with gas from the ventilator.

21. The support arm for use with a respiratory circuit of claim 20, wherein said bladder is configured so as to be selectively connectable to the ventilator for the purpose of being inflated with gas from a compressor line of the ventilator.

22. The support arm for use with a respiratory circuit of claim 18, wherein said control member has an inflation button for inflation of said bladder to effect locking of said arm segments, and said control member has a deflation button for deflation of said bladder to effect unlocking of said arm segments.

23. The support arm for use with a respiratory circuit of claim 19, wherein said respiratory support member has a respiratory support adjustment handle for use in combination with said bladder to effect a locking and unlocking of said respiratory support member with respect to said arm segment.

24. The support arm for use with a respiratory circuit of claim 16, wherein one of said arm segments is configured so as to be adjustably connected to the ventilator by a ventilator connection adjustment handle, said ventilator connection adjustment handle being configured in a manner allowing for adjustment of said arm segment on the ventilator.

25. The support arm for use with a respiratory circuit of claim 16, wherein said flexible section of said arm segment is a corrugated section of interconnected members.

26. The support arm for use with a respiratory circuit of claim 16, wherein said support arm has four arm segments, three of said arm segments are rigid and one of said arm segments has a flexible section, said respiratory support member being attached to said arm segment having a flexible section.

27. The support arm of claim 16, wherein said swivel joints have a snap ring configuration, said snap ring configuration is disengaged during deflation of said bladder and allows said swivel joint to move freely, inflation of said bladder engages said snap ring configuration and locks said swivel joint.

28. A support arm for use with a respiratory support circuit having a ventilator, comprising:
three arm segments, two of said arm segments being a rigid member, the other of said arm segments having a flexible section, one of said rigid arm segments being adjustably connected on one end thereof to the ventilator, said two rigid arm segments being adjustably connected to one another by a first swivel joint, one of said rigid arm segments and said arm segment having said flexible section being adjustably connected to one another by a second swivel joint, said flexible section being formed by a corrugated member;

a respiratory support member connected to said arm segment having said flexible section, said respiratory support member having one end configured for engagement with a tube of a respiratory circuit to support the tube, said respiratory support member having a pivot connection therein to allow for adjustment of said respiratory support member; and a flexible bladder disposed through said arm segments, inflation of said flexible bladder effects a locking of said swivel joints and said flexible section to effect a locking of said arm segments and prevent relative motion between said arm segments, inflation of said bladder effects a locking of said pivot connection of said respiratory support member to prevent adjustment of said respiratory support member.

* * * * *